(12) United States Patent
Lessner et al.

(10) Patent No.: US 7,256,982 B2
(45) Date of Patent: Aug. 14, 2007

(54) ELECTROLYTIC CAPACITOR

(76) Inventors: Philip Michael Lessner, 140 Circle Slope Dr., Simpsonville, SC (US) 29681; Brian Melody, 124 Woody Creek Rd., Greer, SC (US) 29650; John Tony Kinard, 108 Mount Vernon Cir., Greer, SC (US) 29651; Joachim Hossick Schott, 5330 DuPont Ave. South, Minneapolis, MN (US) 55419

( * ) Notice: Subject to any disclaimer, the term of this patent is extended or adjusted under 35 U.S.C. 154(b) by 0 days.

(21) Appl. No.: 10/449,645

(22) Filed: May 30, 2003

(65) Prior Publication Data

US 2004/0240149 A1 Dec. 2, 2004

(51) Int. Cl.
*H01G 9/04* (2006.01)
*H01G 9/145* (2006.01)

(52) U.S. Cl. ............... 361/516; 361/503; 361/508

(58) Field of Classification Search ........ 361/503–521; 607/5
See application file for complete search history.

(56) References Cited

U.S. PATENT DOCUMENTS

| | | |
|---|---|---|
| 3,243,316 A | 3/1966 | O'Nan et al. |
| 3,612,956 A * | 10/1971 | Sterling et al. ............. 361/524 |
| 4,090,231 A | 5/1978 | Millard et al. |
| 4,562,511 A | 12/1985 | Nishino et al. |
| 4,780,794 A | 10/1988 | Mase et al. |
| 4,780,797 A | 10/1988 | Libby |
| 4,910,645 A | 3/1990 | Jonas et al. |
| 4,942,500 A | 7/1990 | Libby et al. |
| 5,043,849 A | 8/1991 | Libby |
| 5,098,485 A | 3/1992 | Evans |
| 5,187,788 A | 2/1993 | Marmelstein |
| 5,312,439 A | 5/1994 | Loeb |
| 5,331,579 A | 7/1994 | Maguire, Jr. et al. |
| 5,369,547 A | 11/1994 | Evans |
| 5,469,325 A | 11/1995 | Evans |
| 5,531,772 A * | 7/1996 | Prutchi ........................ 607/17 |
| 5,541,863 A | 7/1996 | Magor et al. |
| 5,559,667 A | 9/1996 | Evans |
| 5,671,415 A | 9/1997 | Hossain |
| 5,729,427 A | 3/1998 | Li et al. |
| 5,737,181 A | 4/1998 | Evans |
| 5,754,394 A | 5/1998 | Evans et al. |
| 5,786,980 A | 7/1998 | Evans |
| 5,800,706 A | 9/1998 | Fischer |

(Continued)

FOREIGN PATENT DOCUMENTS

DE   30 11 701   10/1981

(Continued)

OTHER PUBLICATIONS

Carlberg et al. "Poly(3,4-ethylenedioxythiophene) as electrode material in electrochemical capacitors", Journal of Electrochemical Society, 1997, 144, pp. L61-L64.*

(Continued)

*Primary Examiner*—Eric W. Thomas
(74) *Attorney, Agent, or Firm*—Foley & Lardner LLP

(57) ABSTRACT

A capacitor is provided which includes a plurality of electrodes and a fluid electrolyte provided to electrically associate the plurality of electrodes. One of the plurality of electrodes includes poly (ethylene 3,4-dioxythiophene) or a titanate.

55 Claims, 3 Drawing Sheets

U.S. PATENT DOCUMENTS

| | | | |
|---|---|---|---|
| 5,822,177 A | 10/1998 | Popp et al. | |
| 5,849,031 A * | 12/1998 | Martinez et al. | 607/121 |
| 5,851,506 A | 12/1998 | Zheng et al. | |
| 5,894,403 A | 4/1999 | Shah et al. | |
| 5,926,362 A | 7/1999 | Muffoletto et al. | |
| 5,932,185 A | 8/1999 | Pekala et al. | |
| 5,980,977 A | 11/1999 | Deng et al. | |
| 5,982,609 A * | 11/1999 | Evans | 361/516 |
| 5,985,112 A | 11/1999 | Fischer | |
| 6,031,711 A | 2/2000 | Tennent et al. | |
| 6,094,339 A | 7/2000 | Evans | |
| 6,099,960 A | 8/2000 | Tennent et al. | |
| 6,099,965 A | 8/2000 | Tennent et al. | |
| 6,128,180 A | 10/2000 | Araki et al. | |
| 6,154,358 A | 11/2000 | Fukaumi et al. | |
| 6,191,931 B1 * | 2/2001 | Paspa et al. | 361/302 |
| 6,203,814 B1 | 3/2001 | Fisher et al. | |
| 6,205,016 B1 | 3/2001 | Niu | |
| 6,208,502 B1 | 3/2001 | Hudis et al. | |
| 6,210,450 B1 | 4/2001 | Fukaumi et al. | |
| 6,221,330 B1 | 4/2001 | Moy et al. | |
| 6,288,890 B1 | 9/2001 | Saito et al. | |
| 6,352,564 B1 | 3/2002 | Araki et al. | |
| 6,356,433 B1 * | 3/2002 | Shi et al. | 361/502 |
| 6,381,121 B1 | 4/2002 | Monden et al. | |
| 6,414,836 B1 | 7/2002 | Tennent et al. | |
| 6,419,717 B2 | 7/2002 | Moy et al. | |
| 6,426,863 B1 | 7/2002 | Munshi | |
| 6,432,866 B1 | 8/2002 | Tennent et al. | |
| 6,442,016 B2 | 8/2002 | Fukuyama et al. | |
| 6,459,565 B1 | 10/2002 | Lessner et al. | |
| 6,491,789 B2 | 12/2002 | Niu | |
| 6,514,897 B1 | 2/2003 | Moy et al. | |
| 6,515,847 B1 | 2/2003 | Naraya | |
| 6,519,137 B1 | 2/2003 | Nitta et al. | |
| 6,674,635 B1 * | 1/2004 | Fife et al. | 361/523 |
| 6,687,118 B1 * | 2/2004 | O'Phelan et al. | 361/508 |
| 2002/0095860 A1 | 7/2002 | Moy et al. | |
| 2002/0146895 A1 * | 10/2002 | Ramdani et al. | 438/497 |
| 2002/0171996 A1 | 11/2002 | Yu et al. | |
| 2003/0035769 A1 | 2/2003 | Moy et al. | |
| 2003/0044519 A1 | 3/2003 | Takai | |
| 2003/0103319 A1 * | 6/2003 | Kumar et al. | 361/312 |
| 2003/0172509 A1 * | 9/2003 | Maletin et al. | 29/25.03 |
| 2004/0064155 A1 | 4/2004 | Norton et al. | |
| 2004/0085711 A1 * | 5/2004 | Merker et al. | 361/523 |
| 2004/0106041 A1 * | 6/2004 | Reynolds et al. | 429/213 |

FOREIGN PATENT DOCUMENTS

| | | | |
|---|---|---|---|
| DE | 198 36 651 A1 | | 2/2000 |
| JP | 03-004512 | | 1/1991 |
| JP | 3-4512 | * | 1/1991 |
| JP | H03-4512 | | 1/1991 |
| JP | 2001-110685 | | 4/2001 |
| JP | 2001-110685 A | * | 4/2001 |
| WO | WO 97/43774 | | 11/1997 |
| WO | WO 00/02213 | | 1/2000 |

OTHER PUBLICATIONS

Sergio Trasatti and Giovanni Buzzanca, "Ruthenium dioxide: a new interesting electrode material. Solid state structure and electrochemical behaviour," Journal of Electroanalytical Chemistry and Interfacial Electrochemistry, 1971, 29, App. 1-5.

Ian D. Raistrick, "Electrochemical Capacitors," Electrochemistry of semiconductors and electronics—processes and devices, eds: John McHardy and Frank Ludwig, 1992, pp. 297-355, Noyes Publications.

G.E. Loeb et al., "Injectable microstimulator for functional electrical stimulation," Med. & Biol. Eng. & Comput., 1991, 29, pp. NS13-NS19.

B.E. Conway, "Electrochemical Supercapacitors" Scientific Fundamentals and Technological Applications, Chapter(s) 9-11, pp. 183-295. 9, Kluwer Academic / Plenum Publishers, no date.

McHardy, et Al., "Electrochemical Supercapacitors and Electronics" Process and Devices, Chapter(s) 9-11, pp. 183-295. 9, Kluwer Academic / Plenum Publishers, no date.

Niu et al., "High power electrochemical capacitors based on carbon nanotube electrodes," Applied Physics Letters 70 (11), Mar. 17, 1997.

Schöenberger et al., "Multiwall carbon nanotubes," Physics World, pp. 37-41 (Jun. 2000).

* cited by examiner

ELECTROLYTIC CAPACITOR

CROSS-REFERENCE TO RELATED PATENT APPLICATIONS

This application is related to Non-Provisional U.S. patent application Ser. No. 10/449,879 entitled "Capacitor And Method For Producing A Capacitor" and Non-Provisional U.S. patent application Ser. No. 10/448,556 entitled "Capacitor And Method For Producing A Capacitor", each of which were filed on the same date as the present application.

BACKGROUND

The present invention relates generally to the field of capacitors. More specifically, the present invention relates to electrolytic capacitors for use in medical devices (e.g., implantable medical devices) or other types of devices.

Since their earliest inception, there has been significant advancement in the field of body-implantable electronic medical devices. Today, such implantable devices include therapeutic and diagnostic devices, such as pacemakers, cardioverters, defibrillators, neural stimulators, drug administering devices, and the like for alleviating the adverse effects of various health ailments.

Implantable medical devices may utilize a capacitor to perform various functions. For example, if the implantable medical device is a defibrillator, one or more capacitors may be used to provide a therapeutic high voltage treatment to the patient.

One type of capacitor that may be used in such an application is an electrolytic or wet slug capacitor. Conventional wet slug capacitors may include a container formed from tantalum or a tantalum alloy that acts as the cathode for the electrolytic capacitor. An electrolyte (e.g., acid such as sulfuric acid) and an anode are provided within the container. In these types of capacitors, a native oxide may be formed on exposed surfaces.

Since the electrolyte is electrically conductive, a conductor-insulator-conductor structure including metal, oxide coating, and electrolyte is present at both the anode and the cathode. Each of these conductor-insulator-conductor structures is itself a capacitor (e.g., an anode capacitor and a cathode capacitor).

In the conventional wet slug capacitor, the anode capacitance is effectively electrically connected in series with the cathode capacitance. The amount of charge at the cathode and anode surfaces are substantially equal and of opposite sign. It should also be noted that the net capacitance of two capacitors connected in series is smaller than the smaller of the capacitances of the two capacitors. Because the oxide layer at the anode of a wet slug capacitor is usually much thicker than the thickness of the oxide layer at the cathode, the anode capacitance of a wet slug capacitor is generally smaller than the cathode capacitance.

The capacitance of a wet slug capacitor can be described using the following equation:

$$C_{Capacitor} = \frac{C_{Cathode} \cdot C_{Anode}}{C_{Cathode} + C_{Anode}}$$

In general, it is desirable to increase the capacitance of the cathode to decrease the risk of forming hydrogen gas at the cathode and to make the capacitance of the anode more clearly observable. Although conventional wet slug capacitors having useful capacitances have been produced, there is a desire to increase the capacitance per unit area and capacitance per unit volume of the cathode coating material. Conventional cathode coating materials (e.g., tantalum), however, may provide a limited capacitance per unit area and limited capacitance per unit volume. For certain applications, it is desirable to provide a capacitor coating material that has a capacitance no less than approximately 10-20 milliFarads per square centimeter.

Accordingly, it is desirable to provide a capacitor that provides one or more of these or other advantageous features. Other features and advantages will be made apparent from the present description. The teachings disclosed extend to those embodiments that fall within the scope of the appended claims, regardless of whether they provide one or more of the aforementioned advantageous.

SUMMARY

Another exemplary embodiment relates to a capacitor comprising a plurality of electrodes and a fluid electrolyte provided to electrically associate the plurality of electrodes. One of the plurality of electrodes comprises poly (ethylene 3,4-dioxythiophene) or a titanate.

Another exemplary embodiment of the invention relates to a capacitor comprising a cathode, an anode, and a fluid electrolyte. The cathode comprises poly (ethylene 3,4-dioxythiophene). The fluid electrolyte is provided to electrically associate the cathode and the anode.

Another exemplary embodiment relates to a capacitor comprising a cathode, an anode, and a fluid electrolyte. The cathode comprises a titanate. The fluid electrolyte is provided to electrically associate the cathode and the anode.

Another exemplary embodiment relates to a medical device comprising an electrolytic capacitor which includes a cathode, an anode, and a fluid electrolyte. The fluid electrolyte electrically associates the cathode and the anode. The cathode comprises poly (ethylene 3,4-dioxythiophene). The medical device is configured to provide a therapeutic high voltage treatment.

Another exemplary embodiment relates to a medical device comprising an electrolytic capacitor which includes a cathode, an anode, and a fluid electrolyte. The fluid electrolyte electrically associates the cathode and the anode. The cathode comprises a titanate. The medical device is configured to provide a therapeutic high voltage treatment.

BRIEF DESCRIPTION OF THE DRAWINGS

The invention will be explained in more detail in the following text using the attached drawings, in which.

DETAILED DESCRIPTION

With reference to the accompanying Figures, the present disclosure relates to capacitors (e.g., electrolytic capacitors, etc.) for use in medical devices (e.g., implantable medical devices, etc.), methods of producing such capacitors, and medical devices which utilize such capacitors. While the subject matter herein is presented in the context of the use of such capacitors in the field of medical devices, such capacitors may be utilized in alternative applications, as will be appreciated by those of skill in the art.

Figure 1:
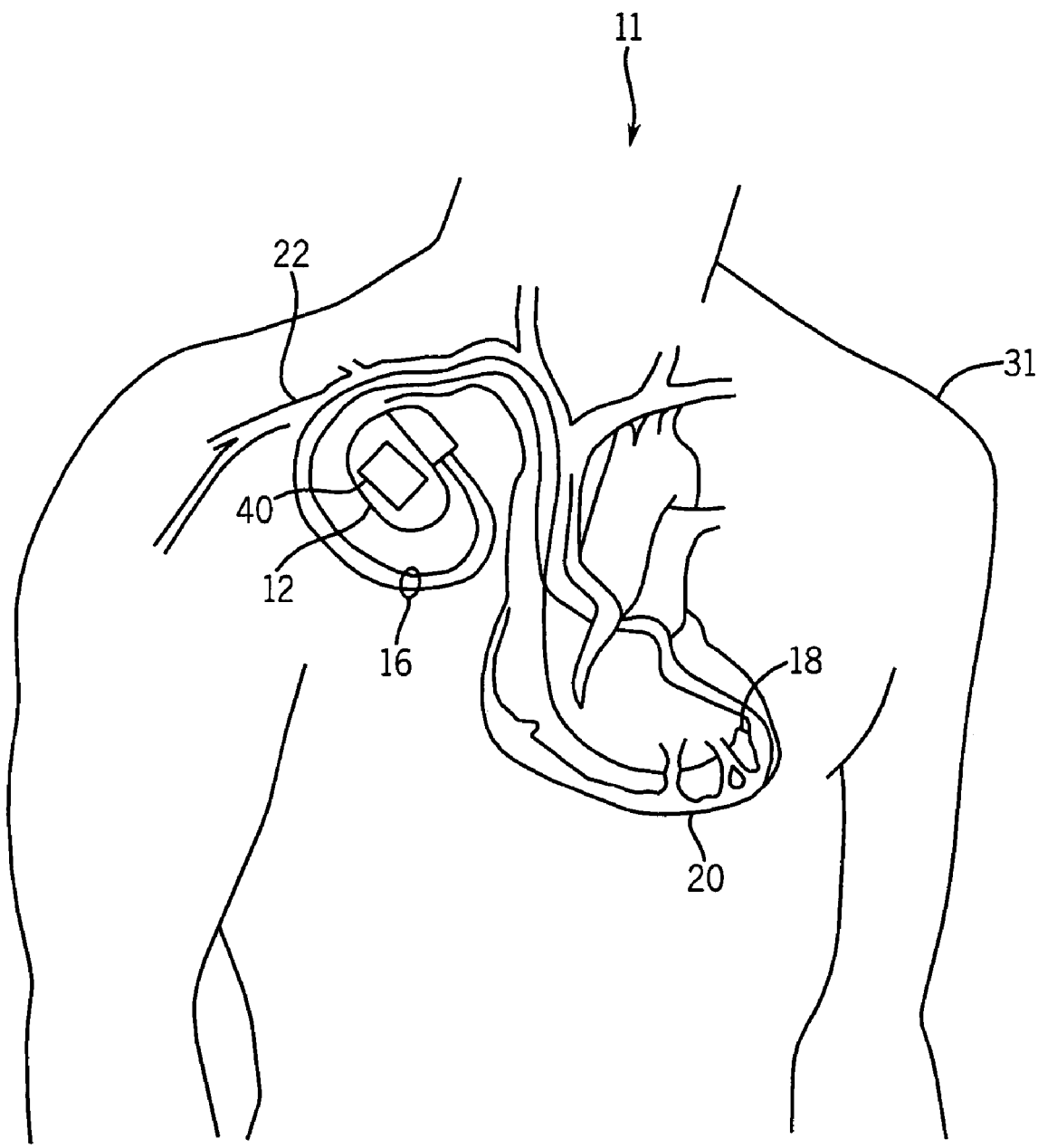
FIG. 1 is a schematic drawing showing an implantable medical device shown in the form of a defibrillator implanted within a human body.

Referring to FIG. 1, a system 11 including an implantable medical device (IMD) is shown as being implanted within a body or torso of a patient 31. The system 11 includes a device 12 in the form of an implantable medical device that for purposes of illustration is shown as a defibrillator. The defibrillator is configured to provide a therapeutic high voltage (e.g., between approximately 500 Volts and approximately 850 Volts, or, desirably, between approximately 600 Volts and approximately 800 Volts) treatment for the patient 31. While the implantable medical device is shown and described as a defibrillator, it should be appreciated that other types of implantable medical devices may be utilized according to alternative embodiments, including but not limited to a pacemaker, cardioverter, neural stimulator, drug administering device, or other implantable medical device. According to still other alternative embodiments, non-implantable medical devices or other types of devices that are not medical devices may utilize capacitors as are shown and described in this disclosure.

The device 12 includes a container or housing that is hermetically sealed and biologically inert according to an exemplary embodiment. The container may be made of a conductive material. One or more leads 16 are electrically coupled between the device 12 and the patient's heart 20 via a vein 22. Cardiac electrodes 18 are provided to sense cardiac activity and/or provide a voltage to the heart 20. At least a portion of the leads 16 (e.g., an end portion of the leads) may be provided adjacent or in contact with one or more of a ventricle and an atrium of the heart 20.

Figure 2:
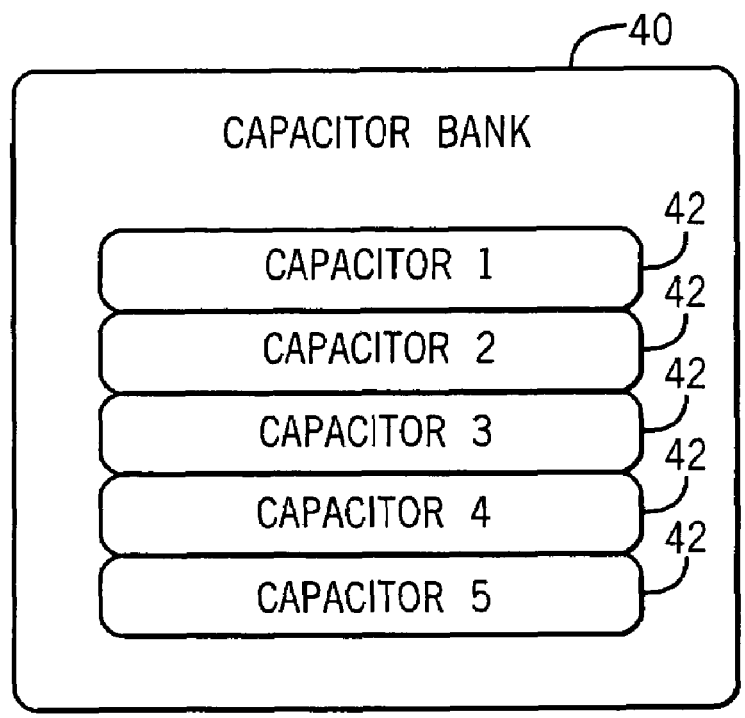
FIG. 2 is a schematic drawing of a capacitor bank that is provided within the implantable medical device shown in FIG. 1.

A capacitor bank 40 including a plurality of capacitors is provided within the device 12. A schematic view of the capacitor bank 40 is shown in FIG. 2, and shows a group of five capacitors 42 connected in series and provided within the capacitor bank 40. The size and capacity of the capacitors 42 may be chosen based on a number of factors, including the amount of charge required for a given patient's physical or medical characteristics. According to other exemplary embodiments, the capacitor bank 40 may include a different number of capacitors 42 (e.g., less than or greater than five capacitors). According to still other exemplary embodiments, a different number of capacitor banks 40 may be provided within the implantable medical device having any suitable number of capacitors 42 provided therein.

Figure 3:
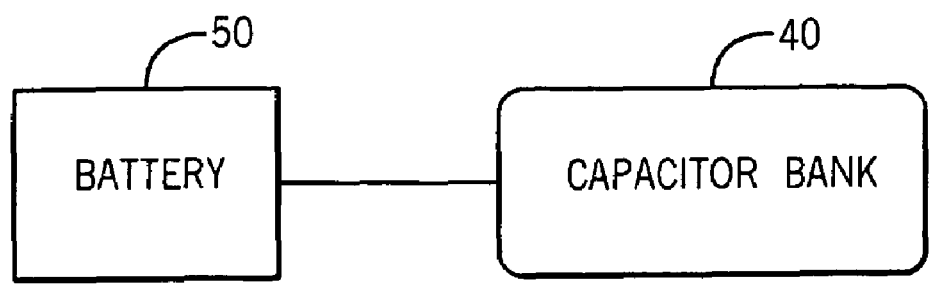
FIG. 3 is a schematic drawing showing the capacitor bank coupled to a battery.

As shown in FIG. 3, the capacitor bank 40 is coupled to a battery 50. According to an exemplary embodiment, the battery 50 is included within the device 12. According to alternative embodiments, the battery may be provided external to the device 12. The capacitors 42 provided within the capacitor bank are configured to store energy provided by the battery 50. For example, the system 11 may be configured such that when the device 12 determines that a therapeutic high-voltage treatment is required to establish a normal sinus rhythm for the heart 20, the capacitors 42 in the capacitor bank 40 are charged to a predetermined charge level by the battery 50. Charge stored in the capacitors 42 may then be discharged via the leads 16 to the heart 20.

According to another exemplary embodiment, the capacitors 42 may be charged prior to determination that a stimulating charge is required by the heart such that the capacitors 42 may be discharged as needed.

In an exemplary embodiment, device 12 is configured to deliver an electric pulse energy to the heart 20 on the order of 30 J for a single defibrillation pulse. However, the energy stored in the capacitors 42 is generally somewhat larger due to losses along the delivery path during the release of the energy. It should be understood that the therapeutic high voltage treatment delivered to the patient's heart 20 may vary somewhat in intensity depending on the patients' physiology and the details of the particular configuration of device 12.

Also, capacitors 42 may be configured to store energy from battery 50 and discharge that energy in a timely manner. For example, capacitors 42 may be configured so that capacitor charge times may be of the order of 10 seconds when using electrical currents of the order of 10 mA. Also, capacitors 42 may be configured so that the typical discharge times are of the order of 10 milliseconds. Thus, in this exemplary embodiment, the capacitors 42 are configured to deliver about 30 J of electrical energy in a total time window of about 10 seconds, using a charge current on the order of 10 mA.

In order to provide these relatively low charge and discharge times, capacitors 42 generally have low internal resistance, or more generally speaking, impedance. The impedance behavior of capacitors 42 is typically characterized by its equivalent series resistance (ESR) value measured at a specified frequency. For capacitor bank 40, the ESR measured at 120 Hz is typically of the order of 5 Ohms or less. Thus, capacitor bank 40 is able to provide timely delivery of the therapeutic high voltage treatment with minimal waste of energy lost in heating the device. It should be understood that other embodiments may have different charging and/or discharging characteristics depending on the needs of the device in which it is used.

Figure 4:
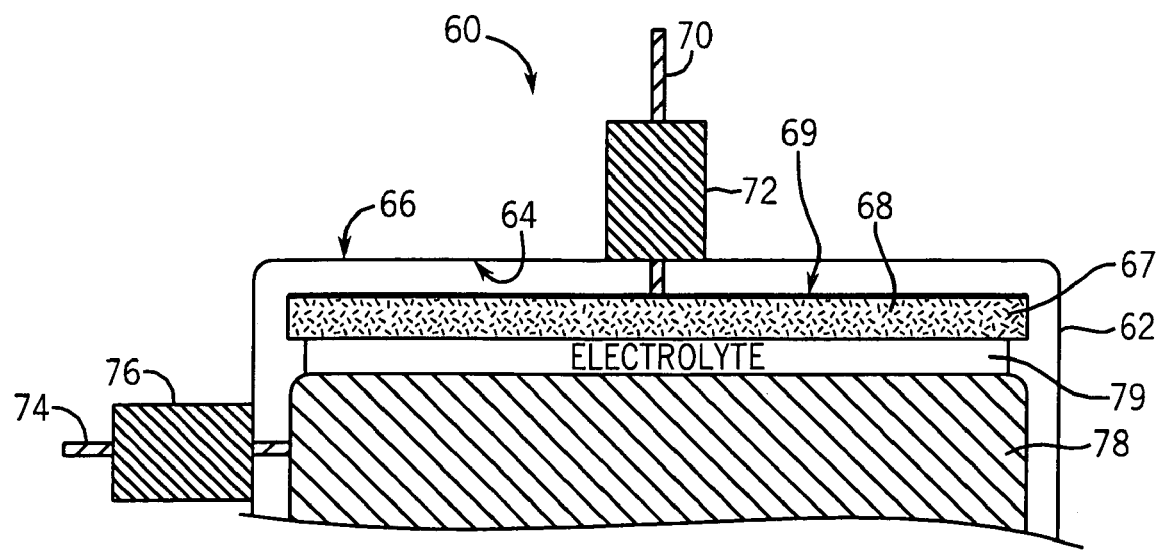
FIG. 4 is a schematic cross-sectional view of one of the capacitors provided within the capacitor bank shown in FIG. 2 according to an exemplary embodiment.

Various types of capacitors may be provided within the capacitor bank 40 according to various exemplary embodiments. FIG. 4 shows a schematic cross-sectional view of a portion of a capacitor 60 according to a first exemplary embodiment. The capacitor 60 includes a container or housing 62 (e.g., a hermetically sealed container). According to an exemplary embodiment, the container comprises titanium. According to other exemplary embodiments, other materials may be used in place of or in addition to titanium (e.g., stainless steel, silver, valve metals such as aluminum, tantalum, niobium, zirconium, alloys of any of the previous materials, etc.). For example, an alloy of titanium/6% aluminum/4% vanadium may be used as the material for container 62. In general, the material or materials used to form the container 62 are chosen based on the particular electrolyte used in the capacitor. Thus, the container 62 comprises a conductive material that resists corrosion from the electrolyte.

Capacitor 60 generally includes a plurality of electrodes (e.g., cathode and anode). As shown in FIG. 4, capacitor 60 includes a cathode 68 that is provided within the container 62. According to an exemplary embodiment, the cathode 68 is electrically isolated from an inner surface 64 of the container 62 and comprises an active or coating material 67 and a substrate 69. According to an exemplary embodiment, substrate 69 comprises titanium. In other exemplary embodiments, substrate 69 may include stainless steel, silver, tantalum, niobium, zirconium, aluminum, alloys of these materials (e.g., Ti/6% Al/4% Va, etc.), etc. A cathode lead 70 is electrically coupled to the cathode 68 and extends through a wall 66 of the container 62. The cathode lead 70 is electrically isolated from the container 62 by a feed-through 72. According to an exemplary embodiment, the feed-through 72 comprises an insulating material (e.g., glass) that seals the cathode lead 70 from the container 62. The feed-through 72 may also act to prevent material (e.g., electrolyte) from escaping the container 62 and to prevent foreign matter from entering the container 62 in the location of the cathode lead 70.

In an exemplary embodiment, the cathode 68 has a specific capacitance that is not less than about 10 milliFarads per square centimeter. In another exemplary embodiment, the cathode 68 has a specific capacitance that is not less than about 20 milliFarads per square centimeter.

An anode 78 is provided within the container 62. According to an exemplary embodiment, the anode 78 comprises tantalum (e.g., a porous sintered tantalum slug). According to other exemplary embodiments, the anode 78 may comprise other materials in addition to or in place of tantalum (e.g. valve metals such as, aluminum, titanium, niobium, zirconium, etc.). The anode 78 is provided in the container 62 such that it is not in direct contact with (e.g., is spaced apart from) the cathode 68. Typically, a separator is used to prevent anode 78 and cathode 68 from touching. The separator can be any of a number of suitable materials (e.g., cellulose, etc.) that separate the anode 78 and cathode 68 as well as allow a sufficient amount of electrolyte to pass through for the capacitor to function properly.

The anode 78 is electrically coupled to an anode lead 74 that passes through a wall 66 of the container 62 via a feed-through 76. The feed-through 76 may be constructed in a similar manner as described with respect to feed-through 72 and may act to electrically isolate the anode lead 74 from the container 62 in substantially the same manner as described with respect to cathode lead 70 and feed-through 72.

A fluid or liquid electrolyte 79 is provided in the container 62. At least a portion of the electrolyte 79 is provided intermediate the cathode 68 and the anode 78. The electrolyte 79 electrically associates cathode 68 and the anode 78. According to an exemplary embodiment, the electrolyte may comprise ammonium salts (e.g., ammonium acetate) dissolved in a water and an organic solvent (e.g., glycol, etc.), phosphoric acid, etc. The particular electrolyte chosen may depend on a number of factors, such as the desired reactivity of the electrolyte with the cathode and anode, compatibility with the material or materials that make up the container 62, desired breakdown voltage, etc.

Figure 5:
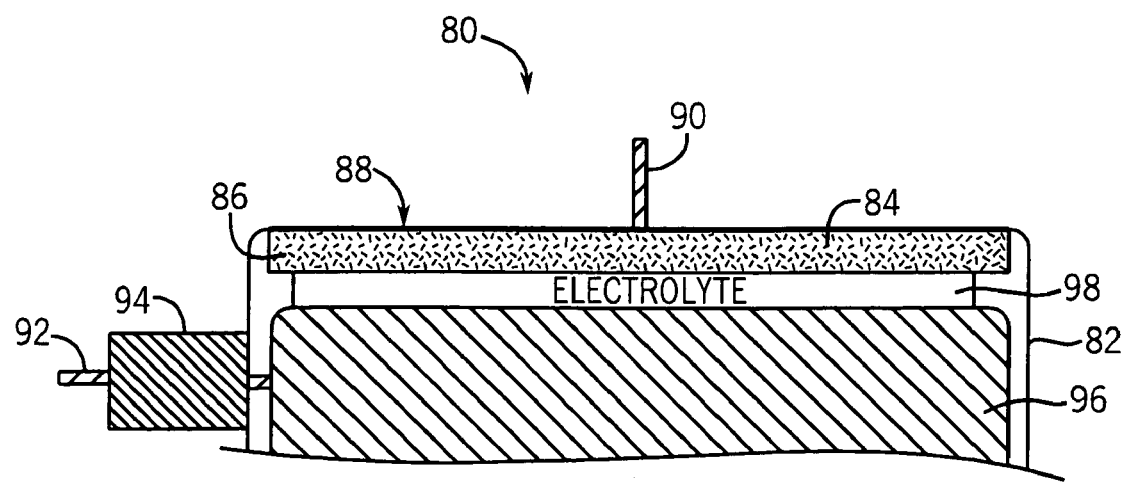
FIG. 5 is a schematic cross-sectional view of one of the capacitors provided within the capacitor bank shown in FIG. 2 according to another exemplary embodiment.

FIG. 5 shows a cross-sectional schematic view of a portion of a capacitor 80 according to a second exemplary embodiment. The capacitor 80 includes a container or housing 82 which may be constructed in a manner similar to that described with respect to the container 62.

A cathode 84 is integrally formed with the container 82 and comprises wall 88 and active or coating material 86. In this embodiment, wall 88 functions as the substrate for active material 86. The cathode 84 is electrically coupled to a cathode lead 90 that extends from the wall 88 of the container 82.

An anode 96 is provided within the container 82 such that the anode 96 is not in contact with (e.g., is spaced apart from) the cathode 84. According to an exemplary embodiment, the anode 78 comprises tantalum. According to other exemplary embodiments, the anode 78 may comprise other materials in addition to or in place of tantalum (e.g., aluminum, titanium, niobium, zirconium, etc.).

The anode 96 is electrically coupled to an anode lead 92 through a feed-through 94. The feed-through 94 may be constructed in a similar manner to that described with respect to the feed-through 72 and the feed-through 76.

The anode 96 and the cathode 84 may be configured in a variety of ways. According to an exemplary embodiment, the anode 96 and the cathode 84 are configured to be similar to the anode 78 and the cathode 68.

A fluid or liquid electrolyte 98 is provided in the container 82. At least a portion of the electrolyte 98 is provided intermediate the cathode 84 and the anode 96 and electrically associates the cathode 84 and the anode 96. The electrolyte 98 utilized in the capacitor 80 may be the same as or may differ from that utilized in the capacitor 60. In general, the same factors considered in choosing the electrolyte 79 also apply in choosing the electrolyte 98.

Referring to FIGS. 4 and 5, the active materials 67 and 86 may comprise a number of materials. In an exemplary embodiment, materials are chosen that have a relatively high capacitance. Generally, materials that have a high capacitance include materials that have a high surface area, have the ability to absorb protons, and/or have a high dielectric constant.

In one exemplary embodiment, the active materials 67 and 86 comprise a conducting polymer such as poly (ethylene 3,4-dioxythiophene) (hereinafter "PEDT"). PEDT is generally a high surface area conductive polymer that is not lamellar. PEDT is a suitable material to use for the active materials 67 and 86 because of its high surface area and ability to absorb protons. PEDT also provides a number of other advantages over other conducting polymers. For example, PEDT is relatively thermally stable up to a temperature of approximately 125 C. Also, PEDT is generally more conductive than other thiophene polymers. While not wishing to be bound by theory, it is thought that PEDT's higher conductivity relative to other thiophene polymers is due to the directing effect of the bonds at the 3,4 positions (i.e., the oxygen bonds at the 3,4 positions prevent PEDT from conducting at those positions so that the 2,5 positions, the only positions readily available for bonding during polymerization, are the positions associated with maximum conductivity).

PEDT may be applied to the substrate 69 or the wall 88 of the container 82 using chemical and/or electrochemical oxidation of the monomer. In an exemplary embodiment, a solution of the monomer and a solvent alcohol (e.g., methanol, ethanol, etc.) is applied to the substrate 69 or the wall 88. The solvent alcohol is evaporated leaving the monomer. A solution of water, an oxdizer (e.g., ammonium persulfates, etc.), and a doping agent (e.g., para-toluene sulfonic acid, etc.) is then applied to the monomer. The monomer reacts with the oxidizer and the doping agent to form poly (ethylene 3,4-dioxythiophene). In an alternative embodiment, the solution of water, oxidizer, and doping agent may be applied to substrate 69 or wall 88 first and then, after evaporating the water, the monomer is applied. Also, the doping agent may be provided in solution with the monomer rather than with the oxidizer. Many methods known by those of ordinary skill in the art can be used to apply the PEDT to the substrate 69 or the wall 88. Thus, PEDT may be applied to the substrate 69 or the wall 88 in any manner that is suitable to provide the desired structure.

In another exemplary embodiment, the active materials 67 and 86 comprise titanates such as titanates that are used in ceramic capacitors. For example, acceptable titanates include, but should not be limited to, alkaline earth titanates (i.e., beryllium titanate, magnesium titanates, calcium titanate, strontium titanate, barium titanate, radium titanate), organic titanates, lead titanate, cadmium titanate, niobium titanate, strontium titanate, etc. Titanates are suitable materials to use for active materials 67 and 86 because typically they have a high dielectric constant and an ability to absorb protons. In an exemplary embodiment, the titanates used have a dielectric constant that is not less than about 50, or, desirably, not less than about 100. For example, barium titantate exhibits a dielectric constant of approximately 1600. Also, titanates are relatively thermally stable up to a temperature of approximately 125 C.

The titanates may be applied to the substrate 69 or the wall 88 of the container 82 in a variety of ways. In an exemplary embodiment, a suspension of water and the titanate or titanates are contacted with the substrate 69 or the wall 88 of the container 82. The suspension is then heated to a temperature sufficient to thermally bond the titanate to the substrate 69 or the wall 88. In another embodiment, the titanate or a precursor, such as barium acetate, is contacted with the substrate 69 or the wall 88 of the container 82. The substrate 69 or the wall 88 and the titanates or titanate precursors are then heated to a sufficient temperature to bond the titanate to the substrate 69 or the wall 88. In an alternative embodiment, the titanates are sputtered, brushed, etc. onto the substrate 69 or the wall 88. The substrate 69 or wall 88 is then heated to bond the titanate(s) to the substrate 69 or wall 88. If the substrate 69 or wall 88 is titanium then the bonding temperature is desirably between approximately 800 C and approximately 1000 C, and the bonding temperature may be at or near the beta transition temperature of titanium (i.e., the temperature at which the structure of the titanium changes from hexagonal to cubic, which is approximately 865 C).

In an exemplary embodiment, the thickness of the active materials 67 and 86 is between approximately 0.025 inches and approximately 0.0001 inches or, desirably, between approximately 0.003 inches and approximately 0.0005 inches. In another exemplary embodiment, the thickness of the active materials 67 and 86 is no more than approximately 0.003 inches.

The anodes 78 and 96 may also include PEDT or titanates in a similar manner and as disclosed with regard to the cathodes 68 and 84. Thus, it should be understood that the use of PEDT and titanates is not limited to the cathodes 68 and 84. Rather, these materials may be used in a variety of desirable configurations in an appropriate capacitor.

As utilized herein, the terms "approximately," "about," and similar terms are intended to have a broad meaning in harmony with the common and accepted usage by those of ordinary skill in the art to which the subject matter of this disclosure pertains. It should be understood by those of skill in the art that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The construction and arrangement of the elements of the capacitor as shown in the preferred and other exemplary embodiments is illustrative only. Although only a few embodiments of the present inventions have been described in detail in this disclosure, those skilled in the art who review this disclosure will readily appreciate that many modifications are possible without materially departing from the novel teachings and advantages of the subject matter recited in the claims. Accordingly, all such modifications are intended to be included within the scope of the present invention as defined in the appended claims. The order or sequence of any process or method steps may be varied or re-sequenced according to alternative embodiments. Other substitutions, modifications, changes and omissions may be made in the design, operating conditions and arrangement of the preferred and other exemplary embodiments without departing from the scope of the present invention as expressed in the appended claims.

What is claimed is:

1. A capacitor comprising:
   a plurality of electrodes;
   a fluid electrolyte provided to electrically associate the plurality of electrodes;
   wherein one of the plurality of electrodes comprises a substrate, which includes a valve metal, and a layer of poly (ethylene 3,4-dioxythiophene) adjacent to the substrate; and one of the plurality of electrodes comprises a dielectric layer.

2. The capacitor of claim 1 wherein the one electrode is the cathode.

3. The capacitor of claim 1 wherein the one electrode further comprises titanium.

4. The capacitor of claim 1 wherein the one electrode comprises a layer of material which includes the poly (ethylene 3,4-dioxythiophene) and has a specific capacitance of at least approximately 10 milliFarads per square centimeter.

5. The capacitor of claim 1 wherein the one electrode comprises a layer of material which includes the poly (ethylene 3,4-dioxythiophene) and the layer of material has a thickness of approximately 0.025 inches to approximately 0.0001 inches.

6. The capacitor of claim 1 wherein the metal comprises titanium.

7. The capacitor of claim 1 wherein the dielectric layer comprises a native oxide.

8. The capacitor of claim 1 wherein the valve metal is selected from the group consisting of titanium, tantalum, stainless steel, aluminum, niobium, zirconium, and alloys thereof.

9. A capacitor comprising:
   a cathode which comprises a substrate, which includes a valve metal, a dielectric layer, and a layer of poly (ethylene 3,4-dioxythiophene) adjacent to the substrate;
   an anode; and
   a fluid electrolyte provided to electrically associate the cathode and the anode.

10. The capacitor of claim 9 wherein the valve metal is selected from a group consisting of titanium, tantalum, stainless steel, aluminum, niobium, zirconium, and alloys thereof.

11. The capacitor of claim 9 wherein the metal comprises titanium.

12. The capacitor of claim 9 wherein the layer of material has a thickness of approximately 0.025 inches to approximately 0.0001 inches.

13. The capacitor of claim 9 wherein the substrate and the layer of material are in contact.

14. The capacitor of claim 9 further comprising a housing, wherein the substrate comprises at least a portion of the housing.

15. The capacitor of claim 9 wherein the layer of material has a thickness of no more than approximately 0.003 inches.

16. The capacitor of claim 9 wherein the cathode comprises a layer of material that has a specific capacitance of at least approximately 10 milliFarads per square centimeter.

17. The capacitor of claim 16 wherein the layer of material has a specific capacitance of at least approximately 20 milliFarads per square centimeter.

18. The capacitor of claim 9 wherein the capacitor is hermetically sealed.

19. The capacitor of claim 9 wherein the anode comprises tantalum.

20. The capacitor of claim 9 wherein the dielectric layer comprises a native oxide.

21. The capacitor of claim 9 wherein the valve metal is selected from the group consisting of titanium, tantalum, stainless steel, aluminum, niobium, zirconium, and alloys thereof.

22. A capacitor comprising:
a cathode which comprises a titanate;
an anode; and
a fluid electrolyte provided to electrically associate the cathode and the anode.

23. The capacitor of claim 22 wherein the titanate has a dielectric constant of at least approximately 50.

24. The capacitor of claim 22 wherein the titanate has a dielectric constant of at least approximately 100.

25. The capacitor of claim 22 wherein the cathode comprises a layer of material that has a specific capacitance of at least approximately 10 milliFarads per square centimeter.

26. The capacitor of claim 25 wherein the layer of material has a specific capacitance of at least approximately 20 milliFarads per square centimeter.

27. The capacitor of claim 22 wherein the cathode comprises:
a substrate, which includes a metal; and
a layer of material provided adjacent to the substrate, the layer of material comprising the titanate.

28. The capacitor of claim 27 wherein the metal is selected from a group consisting of titanium, tantalum, niobium, and zirconium, and alloys thereof.

29. The capacitor of claim 27 wherein the layer of material and the substrate are in contact.

30. The capacitor of claim 27 wherein the layer of material and the substrate are heated to a temperature not less than approximately 800° C. to bond the layer of material to the substrate.

31. The capacitor of claim 30 wherein the metal comprises titanium.

32. The capacitor of claim 22 wherein the titanate is selected from a group consisting of alkaline earth titanates and mixtures thereof.

33. The capacitor of claim 22 wherein the anode comprises tantalum.

34. A medical device comprising:
an electrolytic capacitor including a cathode, an anode, and a fluid electrolyte, the fluid electrolyte electrically associating the cathode and the anode;
wherein the cathode comprises a substrate, which includes a valve metal, a dielectric layer, a layer of poly(ethylene 3,4-dioxythiophene) adjacent to the substrate; and
wherein the medical device is configured to provide a therapeutic high voltage treatment.

35. The medical device of claim 34 wherein the medical device is configured to be implanted in the body of a human.

36. The medical device of claim 34 wherein the metal includes titanium.

37. The medical device of claim 36 wherein the substrate and the layer of material are in contact.

38. The capacitor of claim 34 wherein the dielectric layer comprises a native oxide.

39. The capacitor of claim 34 wherein the valve metal is selected from the group consisting of titanium, tantalum, stainless steel, aluminum, niobium, zirconium, and alloys thereof.

40. A medical device comprising:
an electrolytic capacitor including a cathode, an anode, and a fluid electrolyte, the fluid electrolyte electrically associating the cathode and the anode;
wherein the cathode comprises a titanate;
wherein the medical device is configured to provide a therapeutic high voltage treatment.

41. The medical device of claim 40 wherein the cathode comprises:
a substrate, which includes a metal;
a layer of material provided adjacent to the substrate, the layer of material comprising the titanate.

42. The medical device of claim 41 wherein the medical device is configured to be implanted in the body of a human.

43. The medical device of claim 41 wherein the metal includes titanium.

44. The medical device of claim 43 wherein the substrate and the layer of material are in contact.

45. The medical device of claim 40 wherein the titanate has a dielectric constant of at least approximately 50.

46. The medical device of claim 45 wherein the titanate has a dielectric constant of at least approximately 100.

47. The medical device of claim 40 wherein the titanate is selected from a group consisting of alkaline earth titanates and mixtures thereof.

48. A capacitor comprising:
a plurality of electrodes;
a fluid electrolyte provided to electrically associate the plurality of electrodes; and
wherein one of the plurality of electrodes comprises poly(ethylene 3,4-dioxythiophene), a dielectric layer, and a valve metal.

49. The capacitor of claim 48 wherein the one electrode is the cathode.

50. The capacitor of claim 48 wherein the one electrode comprises aluminum, titanium, niobium, zirconium, or alloys thereof.

51. The capacitor of claim 48 wherein the one electrode comprises titanium.

52. A medical device which includes the capacitor of claim 48.

53. The medical device of claim 52 wherein the medical device is configured to provide a therapeutic high voltage treatment.

54. The capacitor of claim 48 wherein the dielectric layer comprises a native oxide.

55. The capacitor of claim 48 wherein the valve metal is selected from the group consisting of titanium, tantalum, stainless steel, aluminum, niobium, zirconium, and alloys thereof.

* * * * *